US007629502B2

(12) United States Patent
Chan

(10) Patent No.: US 7,629,502 B2
(45) Date of Patent: Dec. 8, 2009

(54) NON-ANTIBIOTIC SELECTION MARKER GENES

(75) Inventor: Ming-Tsair Chan, Taipei (TW)

(73) Assignee: Academia Sinica, Nan-Kang, Taipei (TW)

( * ) Notice: Subject to any disclaimer, the term of this patent is extended or adjusted under 35 U.S.C. 154(b) by 11 days.

(21) Appl. No.: 11/635,286

(22) Filed: Dec. 7, 2006

(65) Prior Publication Data

US 2008/0141391 A1 Jun. 12, 2008

(51) Int. Cl.
*C12N 15/82* (2006.01)
*C12N 15/29* (2006.01)
*C12N 15/55* (2006.01)

(52) U.S. Cl. ...................... 800/278; 536/23.6; 435/195; 435/320.1; 435/431; 435/468

(58) Field of Classification Search ........................ None
See application file for complete search history.

(56) References Cited

U.S. PATENT DOCUMENTS

| 5,278,057 | A  | * | 1/1994  | Jorgensen ................... 800/266 |
|-----------|----|---|---------|--------------------------------------|
| 7,045,678 | B2 | * | 5/2006  | Chiu .......................... 800/18 |
| 2002/0061570 | A1 | * | 5/2002  | Anderson et al. ........... 435/193 |
| 2002/0168709 | A1 | * | 11/2002 | Hennecke et al. .......... 435/69.1 |

OTHER PUBLICATIONS

Last, et al., (1991). Tryptophan mutants in *Arabidopsis*: the consequences of duplicated tryptophan synthase beta genes. Plant Cell 3: 345-358.*
Barczak et al, 5-Fluoroindole resistance identifies tryptophan synthase beta subunit mutants in *Arabidopsis thaliana*. Genetics, (May 1995) vol. 140, No. 1, pp. 303-313.*
Weber-Ban, Investigation of allosteric linkages in the regulation of tryptophan synthase: the roles of salt bridges and monovalent cations probed by site-directed mutation, optical spectroscopy, and kinetics. Biochemistry, (Mar. 27, 2001) vol. 40, No. 12, pp. 3497-3511.*
Hyde, et al, 1988, Three-dimensional structure of the tryptophan synthase α2β2 multienzyme complex from *Salmonella typhimurium* J. Biol. Chem. 263: 17857-17871.*
www.mcb.arizona.edu/tax/2010/vector.cfm?id=pBIN 19.*
Avonce, N., Leyman, B., Mascorro-Gallardo, J.O., Van Dijck, P., Thevelein, J.M., and Iturriaga, G (2004). The *Arabidopsis* trehalose-6-P synthase AtTPS1 gene is a regulator of glucose, abscisic acid, and stress signaling. *Plant Physiol* 136, 3649-3659.
Breitler, J.C., Meynard, D., Van Boxtel, J., Royer, M., Bonnot, F., Cambiliau, L., and Guiderdoni, E. (2004). A novel two T-DNA binary vector allows efficient generation of marker-free transgenic plants in three elite cultivars of rice (*Oryza sativa* L.). *Transgenic Res* 13, 27 1-287.
Chan YL, Lin KH, Sanjaya, Liao LJ, Chen WH, Chan MT (2005). Gene stacking in *Phalaenopsis* orchid enhances dual tolerance to pathogen attack. *Transgenic Res* 14:279-288.

Cho, H.J., Brotherton, J.E., and Widholm, J.M. (2004). Use of the tobacco feedback-insensitive anthranilate synthase gene (ASA2) as a selectable marker for legume hairy root transformation. *Plant Cell Rep* 23, 104-113.
Cho, H.J., Brotherton, J.E., Song, H.S., and Widholm, J.M. (2000). Increasing tryptophan synthesis in a forage legume *Astragalus sinicus* by expressing the tobacco feedback-insensitive anthranilate synthase (ASA2) gene. *Plant Physiol* 123, 1069-1076.
Clough, S.J., and Bent, A.F. (1998). Floral dip: a simplified method for Agrobacterium-mediated transformation of *Arabidopsis thaliana. Plant J* 16, 735- 743.
Daniell H, Muthukumar B, Lee SB (2001a) Marker free transgenic plants: engineering the chloroplast genome without the us of antibiotic selection. *Curr Genet* 39:109-116.
Daniell H, Wiebe PO, Millan AF (2001a) Antibiotic-free chloroplast genetic engineering—an environmentally friendly approach. *Trends Plant Sci* 6:237-239.
de Vetten, N., Wolters, A.M., Raemakers, K., van der Meer, I., ter Stege, R., Heeres, E., Heeres, P., and Visser, R. (2003). A transformation method for obtaining marker-free plants of a cross-pollinating and vegetatively propagated crop. *Nat Biotechnol* 21, 439-442.
Ebmeier, A., Allison, L., Cerutti, H., and Clemente, T. (2004). Evaluation of the *Escherichia coli* threonine deaminase gene as a selectable marker for plant transformation. *Planta* 218, 751-758.
Edlund, A., Ekiof, S., Sundberg, B., Moritz, T., and Sandberg, G (1995). A Microscale Technique for Gas Chromatography—Mass Spectrometry Measurements of Picogram Amounts of Indole-3-Acetic Acid in Plant Tissues. *Plant Physiol* 108, 1043-1047.
Erikson, 0., Hertzberg, M., and Nasholm, T. (2004). A conditional marker gene allowing both positive and negative selection in plants. *Nat Biotechnol* 22, 455-458.
Erikson, 0., Hertzberg, M., and Nashoim, T. (2005). The dsdA gene from *Escherichia coli* provides a novel selectable marker for plant transformation. *Plant Mol Biol* 57, 425-433.
Haldrup, A., Petersen, S., and Okkels, F. (1998a). Plant xylose isomerase gene from *Thermoanaerobacterium thermosulfurogenes* allows efective selection of transgenic plant cells using D-xylose as the selection agent. *Plant Mol Biol* 37, 287-296.
Haldrup, A., Petersen, S.G, and Okkels, F.T. (1998b). Positive selection: a plant selection principle based on xylose isomerase, an enzyme used in the food industry. *Plant Cell Rep* 18:76-81.
Hsieh, T.H., Lee, J.T., Charng. Y.Y., and Chan, M.T. (2002a). Tomato plants ectopically expressing *Arabidopsis* CBF 1 show enhanced resistance to water deficit stress. *Plant Physiol* 130, 618-626.
Hsieh, T.H., Lee, J.T., Yang, P.T., Chiu, L.H., Charng, Y.Y., Wang, Y.C., and Chan, M.T. (2002b). Heterology expression of the *Arabidopsis* C-repeat/dehydration response element binding factor 1 gene confers elevated tolerance to chilling and oxidative stresses in transgenic tomato. *Plant Physiol* 129, 1086-1094.

(Continued)

*Primary Examiner*—David T Fox
(74) *Attorney, Agent, or Firm*—Cohen Pontani Lieberman & Pavane LLP

(57) ABSTRACT

The present invention provides for a DNA construct comprising a promoter, a TSB1 gene, and a genetic modification, wherein the TSB1 gene and the genetic modification are promoted by the same said promoter. Additionally, the present invention provides for a plant that is transfected by this DNA construct, and a method of selecting this transfected plant.

6 Claims, 7 Drawing Sheets

OTHER PUBLICATIONS

Hull, A.K., Vij, R., and Celenza, J.L. (2000). *Arabidopsis* cytochrome P450s that catalyze the first step of tryptophan-dependent indole-3-acetic acid biosynthesis. *Proc Natl Acad Sci U S A* 97, 2379-2384.

Joersbo, M. (2001). Advances in the selection of transgenic plants using non-antibiotic marker genes. *Physiologia Plantarum* 111, 269-272.

Kanno, T., Kasai, K., Ikejiri-Kanno, V., Wakasa, K., and Tozawa, V. (2004). In vitro reconstitution of rice anthranilate synthase: distinct functional properties of the alpha subunits OASAI and OASA2. *Plant Mol Biol* 54, 11-22.

Kisaka H, Kisaka M, Lee HY, Kmeya T (1998) Isolation of a cDNA for tryptophan synthase β from rice and studies of its expression in a 5-methyltryptophan-resistant mutant of rice. *Plant Mol Biol* 38:875-878.

Last, R.L., Bissinger, P.H., Mahoney, D.J., Radwanski, E.R., and Fink, GR. (1991). Tryptophan mutants in *Arabidopsis*: the consequences of duplicated tryptophan synthase beta genes. *Plant Cell* 3, 345-358.

Leyman, B., Avonce, N., Ramon, M., Van Dijck, P., Thevelein, J.M., and Iturriaga, G- (2004). New selection marker for plant transformation. *Methods Mol Biol* 267, 385-396.

Leyman, B., Avonce, N., Ramon, M., Di] ck, P.V., Iturriaga, G, and Thevelein, J.M. (2005). Trehalose-6-phosphate synthase as an intrinsic selection marker for plant transformation. *J Biotechnol*.

Liao, L.-J., Pan, I.C., Chan, Y.-L., Hsu, Y.-H., Chen, W.-H., and Chan, M.-T. (2004). Transgene silencing in *Phalaenopsis* expressing the coat protein of Cymbidium Mosaic Virus is a manifestation of RNA-mediated resistance. *Molecular Breeding* 13:229-242.

Mentewab A, Stewart CN Jr (2005) Overexpression of an *Arabidopsis thaliana* ABC trasporter confes kanamycin resistance to transgenic plants. *Nat Biotechnol* 23:1177-1180.

Miki, B., and McHugh, 5. (2004). Selectable marker genes in transgenic plants: applications, alternatives and biosafety. J Biotechnol 107:193-232.

Pomponi M, Censi V, Di Girolamo V, De Paolis A, di Toppi LS, Aromolo R, Costantino P, Cardarelli M (2006) Overexpression of *Arabidopsis phytochelatin* synthase in tobacco plants enhances Cd(2+) tolerance and accumulation but not translocation to the shoot. *Planta* 223:180-190.

Pruitt, K.D., and Last, R.L. (1993). Expression patterns of duplicate tryptophan synthase beta genes in *Arabidopsis thaliana*. *Plant Physiol* 102, 10 19-1026.

Taulavuori, K., Prasad, M.N., Taulavuori, E., and Lame, K. (2005). Metal stress consequences on frost hardiness of plants at northern high latitudes: a review and hypothesis. *Environ Pollut* 135, 209-220.

Tian L, Jordan M, Miki B (2006) Markers ad selector genes for plant transformation. In: Jaime A Teixeira da Silva (eds) Ornamental an plant biotechnology, vol. II. *Global Science Books*, London, pp. 9-20.

Tian L (2006) Markers gene removal from transgenic plants. In: Jaime A Teixeira da Silva (eds) Ornamental and plant biotechnology, vol. II. *Global Science Books*, London, pp. 26-29.

Tozawa, Y., Hasegawa, H., Terakawa, T., and Wakasa, K. (2001). Characterization of rice anthranilate synthase alpha-subunit genes OASAI and OASA2. Tryptophan accumulation in transgenic rice expressing a feedback-insensitive mutant of OASAI. *Plant Physiol* 126, 1493-1506.

Tsai, F.Y., Brotherton, J.E., and Widholm, J.M. (2005). Overexpression of the feedback-insensitive anthranilate synthase gene in tobacco causes tryptophan accumulation. *Plant Cell Rep* 23, 548-556.

Wenck, A., and Hansen, G (2005). Positive selection. Methods Mol Biol 286, 227-236.

You SJ, Liau CH, Hauang HE, Feng TY, Prasad V, Hsiao HH, Lu JC, Chan MT (2003) Sweet pepper ferredoxin-likeprotein (pflp) gene as a novel selection marker for orchid transformation. *Planta* 217:60-65.

Zhao, Y., Christensen, S.K., Fankliauser, C., Cashman, J.R., Cohen, J.D., Weigel, D., and Chory, J. (2001). A role for flavin monooxygenase-like enzymes in auxin biosynthesis. *Science* 291, 306-309.

\* cited by examiner

NON-ANTIBIOTIC SELECTION MARKER GENES

BACKGROUND OF THE INVENTION

Despite the recent advances in the plant transformation systems, the proportion of totipotent cell that become transformed is very low as compared with non transformed cells. Therefore, purpose of an effective selectable marker, antibiotic or herbicide resistant gene is essential to simplify' the detection procedures in order to pick out putatively transformed plants (Leyman et al., 2004; Mild and McHugh, 2004). In general the existing selection systems can be divided mainly into two groups; the conventional selection systems constitute largest group and relay on an antibiotic or herbicide selective agent being detoxified by selective gene. The other group comprises positive selection systems where selective agent is converted into a simple compound by the selective gene product and transformed cells experience metabolic or developmental advantages (Erikson et al., 2004; Wenck and Hansen, 2005).

Currently more than fifty different selection systems have been reported but only few have been popular and reached practical application. Examples are those that use npt II, hpt and bar genes to develop the first generation of transgenic crops regardless of the tissue systems (Haldrup et al., 1998a; Mild and McHugh, 2004), confers antibiotic resistance along with the gene of interest. However, these techniques still need to become more precise to avoid the inadvertent introduction of undesirable genes, such as those carrying allergenicity or those that can cause weediness and endanger natural ecosystems (Daniell et al. 2001b).

In the recent past, alternatively new less controversial selection systems have been developed which no longer result in the presence of resistance genes in the transgenic plants and require nontoxic selective chemicals, such as xylA, galT and dsdA genes mediating selection on xylose, galactose and D-serine, respectively, and providing the transgenic shoots with a metabolic ascendancy over non-transgenic shoots (Haldrup et al., 1998a; Erikson et al., 2005). Although these systems provide a convenient new selection strategy, they do rely on performance of transgenic tissue/shoots. Moreover, most of these marker genes are bacterial in origin and introduction of such genes into foodstuffs raise ethical issues and has caused unforeseen apprehension among the public (Leyman et al., 2004; Erikson et al., 2005). The recovery of marker-free plants with out the necessity sexual crossing is certainly an advantage, however, complete removal of the markers has hindered swift acceptance of these methods (Breitler et al., 2004; Miki and McHugh, 2004). Recently, in potato demonstrated transformation devoid of selectable marker gene (de Vetten et al., 2003), however selection procedure is tedious and consists of many PCR reactions.

Development of an environmentally friendly marker assisted selection system involving natural plant material is gaining momentum. The overexpression of *Arabidopsis* Trehalose-6-phosphate synthase (AtTPS1) gene in *Arabidopsis* and tobacco demonstrated the potential application of this gene in plant transformation (Avonce et al., 2004; Leyman et al., 2004; Leyman et al., 2005).

Tryptophan (Trp), one of the essential amino acid present in the plants, is not synthesized by animals and is the major contributor the indole ring for the synthesis of auxins, glucosinolates, nicotinic acid, phytoalexins and alkaloids (Pruitt and Last, 1993). Biosynthesis of Trp in plants is not constitutive and hence it is produced as and when required. Although the tryptophan biosynthetic pathway is primarily derived from bacteria and fungi, the real biochemistry and mechanism of Trp synthesis and its regulation in plant became well understood only after the innovation of *Arabidopsis* mutants trp1-1, trp2-1 (Last et al., 1991; Pruitt and Last, 1993) and yucca (Zhao et al., 2001) and yeast cDNA screening (Hull et al., 2000). Two genes, *Arabidopsis thaliana* tryptophan synthase beta 1 (AtTSB1 and AtTSB2, encode the tryptophan beta subunit in *Arabidopsis*. Even though both are highly conserved, AtTSB1 mRNA is more abundant than that of AtTSB2 in the leaf tissues (Pruitt and Last, 1993). Hence, the AtTSB1 gene in plants plays a key role in Trp biosynthesis pathway in converting the indole and serine into Trp (Last et al., 1991). Some of the genes that encode certain key enzymes involved in Trp biosynthetic pathway, such as Anthranilate synthase gene (ASA2), in forage legume *Astragalus sinicus* (Cho et al., 2000) and QASA 1 and OASA2 in rice have been characterized (Tozawa et al., 2001; Kanno et al., 2004).

Recent studies showed that overexpression of tobacco feedback-insensitive ASA2 gene in soybean and tobacco increased free Trp levels in transgenic plants and displayed resistance to the toxic Trp analog 5-methyl-tryptophan (5MT) and α-methyltryptophan (αMT), respectively (Cho et al., 2004; Tsai et al., 2005). 5MT binds specifically to an allosteric site on Anthranilate synthase (ASA) catalytic α-subunit and causes interference in cellular Trp synthesis (Zhao et al., 2001; Cho et al., 2004).

SUMMARY OF THE INVENTION

In the present invention, we developed the practical applicability of AtTSB1 gene as a novel selection marker in plant transformation and a simple and efficient 5MT and/or heavy metal-resistant selection procedure.

One embodiment of the present invention is a DNA construct comprising a promoter, a TSB1 gene, and a genetic modification, wherein the TSB1 gene and the genetic modification are promoted by the same said promoter.

The promoter in this DNA construct is preferably the cauliflower mosaic virus 35S promoter. The genetic modification can be, for example, the insertion of Tnos (nopaline synthase terminator sequence).

A second embodiment of the present invention is a plant that is transfected by the DNA construct comprising a promoter, a TSB1 gene, and a genetic modification, wherein the TSB1 gene and the genetic modification are promoted by the same said promoter.

A third embodiment of the present invention is a method of selecting a plant transfected with a DNA construct comprising a promoter, a TSB1 gene, and a genetic modification, wherein the TSB1 gene and the genetic modification are promoted by said promoter, comprising the steps of:

treating a plant with a composition comprising 5MT (5 methyl tryptophan) or CdCl2 or mixture thereof; and determining
a) whether the plant survives;
b) whether the treated plant's tryptophan synthase activity is greater compared to the wild type plant treated with the same composition; or
c) whether the treated plant's free tryptophan concentration is greater compared to the free tryptophan concentration in the wild type plant.

A fourth embodiment of the present invention is a method of selecting a plant transfected with a DNA construct comprising a promoter, a TSB1 gene, and a genetic modification, wherein the TSB1 gene and the genetic modification are promoted by the same said promoter comprising a) assaying for increased tryptophan synthase activity of the plant compared to wild type tryptophan synthase activity; or b) assaying for increased free tryptophan concentration in the plant compared to the free tryptophan concentration in the wild type plant.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

Figure 1:
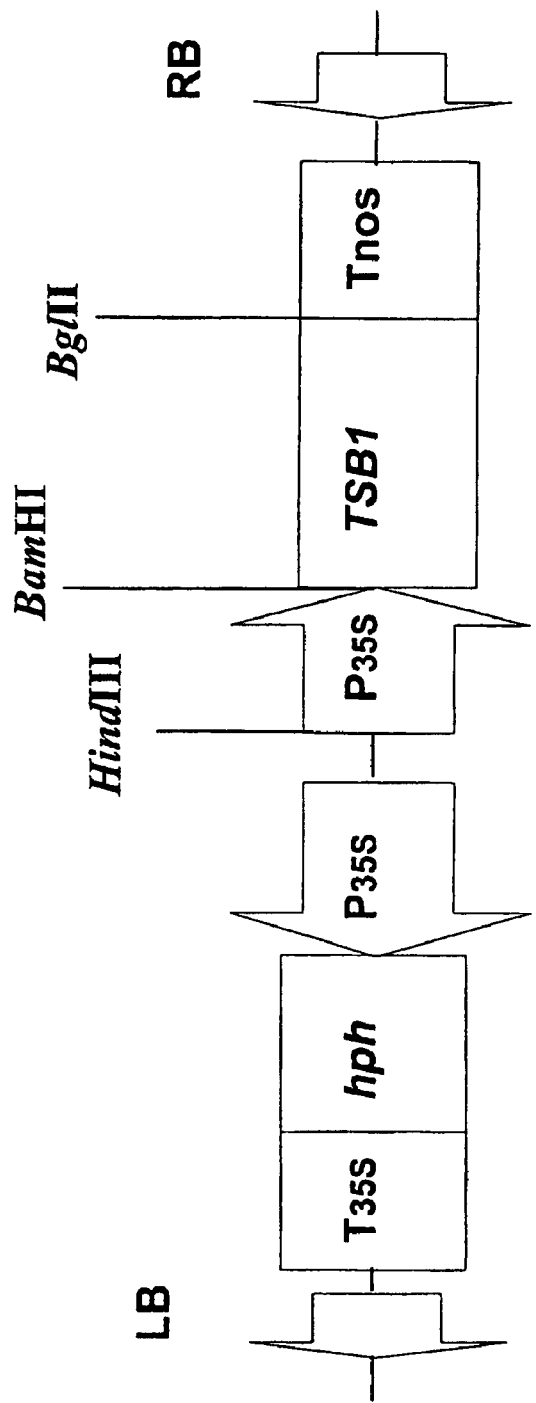
FIG. 1. Schematic representation of pTSB. AtTSB1 Arabidopsis tryptophan synthase beta 1 cDNA, hpt hygromycin phosphotransferse cDNA sequence, P35S CaMV 35S promoter, Tnos nopaline synthase terminator sequence, T35S CaMV 35S terminator sequences, LB left boder, RB right boder.

In developing a new selection system we cloned the AtTSB1 gene to overproduce and accumulate free Trp in transgenic Arabidopsis plants. Resistance to Trp analogue 5MT and heavy metal $CdCl_2$ appears to be accomplished by the overproduction of free Trp, which reduces the effective concentration of the analogue and heavy metal, and is an effective non-antibiotic selectable marker after transformation, equivalent to hygromycin selection. However, the use of antibiotic resistance markers has been the target of societal concerns, because of possible deleterious effect on other organisms in the ecosystem caused by the use of antibiotics, there is a need to develop new markers for risk-free genetic engineering strategies in crop improvement (Mild and McHugh, 2004).

Various positive plant selection systems have been reported utilizing toxic selection agents and marker genes derived from other organisms (Haldrup et al., 1998b; Joersbo, 2001; Ebmeier et al., 2004; Leyman et al., 2004), in these systems the decaying untransformed cells may inhibit the growth of living transformed cells by secreting inhibitors or blocking essential nutrients supply. However, inserting a selection marker gene derived from microorganism into foodstuffs may raise ethical questions and invoke safety concerns. By employing a noncontroversial native selectable marker gene from plants, these practical impediments could be successfully overcome (Leyman et al., 2004). The distinguishing feature of our newly developed TSB1 selection system is that carryover effects were not observed in the plants selected by 5MT or $CaCl_2$. Although antibiotic resistance as a selectable marker may often result in the growth of transformed plants being hampered by selective agent, difficulties in rooting and retarded growth occur even after transplantation to soil (Ebmeier et al., 2004).

The putative transformants in our system survived the 5MT (75 µM) and $CdCl_2$ (300 µM) selection, but non-transformed plants deteriorated on the medium containing the optimal concentration of these selection agents. The transgenic nature of plants selected was further confirmed by Southern and Northern blotting analysis and confirmed the integration and transcriptional expression of plant derived AtTSB1 gene in the genome of transgenic plants (FIGS. 5, 6). The selection effectiveness and efficiency of a selection system relies on the appropriate level of marker gene expression (Tian 2006). In one embodiment of the present invention, transgenic plants selected on 5MT and $CdCl_2$ displayed a high level of TSB1 mRNA transcripts. Thus, selection pressure is mainly due to sufficient expression of the AtT-SB1 marker gene. However, the level of hpt mRNA transcripts was not uniform among the transgenic plants selected by 5MT (FIG. 6a). These observations clearly indicated that the selection pressure is hygromycin independent. The possibility that transgenic plants might express low-levels of AtTSB1 transcripts in the hygromycin selection system may not be ruled out.

The ultimate success of any selection system is being able to rely on quick, clear cut identification of transformants. Our experiments revealed that selection efficiency in the hygromycin and TSB systems are almost the same. However, unlike conventional negative selection systems, our TSB selection system can be effectively employed in routine plant transformation experiments. Indeed, selection efficiency might be considerably increased by utilizing optimal culture conditions depending on the plant species.

Engineering the AtTSB1 gene to overproduce and accumulate Trp for its greater availability and multi-flux distribution is an important step in metabolomics. All the selected transgenic plants by 5MT or $CdCl_2$ showed more free Trp content than wild-type plants. As a consequence of AtTSB1 overexpression, the transgenic plants produce free Trp in the cell compartments and hence were resistance to 5MT or $CdCl_2$. However, this mechanism may not be exists in wild-type counterparts, hence their turning pale green and subsequently death due to destruction of proteins involved in Trp biosynthesis. In concordance with our observations, the forage legume and tobacco plants transformed with tobacco feedback-insensitive Anthranilate synthase (ASA2) gene accumulated higher free Trp content, impart resistant to 5MT, and further demonstrated the importance of ASA2 gene as selection marker (Cho et al., 2000; Tsai et al., 2005).

It is well known fact that heavy metals generally change the membrane properties directly by increasing active oxygen species (Taulavuori et al., 2005). Excess of cadmium ($Cd^{2+}$) in the selection medium (300 μM) may induced changes in oxidative stress and water status and also increase the ratio of chlorophyll a/b in plants. Our results demonstrate that AtTSB1 overexpression in *Arabidopsis* increases Trp content and enhances $Cd^{2+}$ tolerance.

The increase in the free Trp level does not influence the metabolism at cellular level nor whole plant growth, only the capacity to tolerate $Cd^{2+}$ is increased. In addition to its use as a selection marker, AtTSB1 gene can also useful for the generation of crops with increased free Trp content and the ability to be cultivated in heavy metal polluted soils. There appears to be no significant difference in IAA content observed in AtTSB1 transgenic plants and wild-types. This may be the possible reason why there were no adverse side-effects such as abnormal morphological phenotypes were observed.

In summary, the overexpression of AtTSB1 gene in *Arabidopsis* increased the production of free Trp. When the plants were challenged with 5MT or $CdCl_2$ only the transgenic plants are survived, whilst non-transformed plants deteriorated and died due to the inhibitory effect of the selection agents. The selection efficiency in TSB system is almost the same as in hygromycin and selected transgenic plants are normal in morphology and growth.

Materials and Methods

Plasmid Construction

An AtTSB1 gene was isolated by reverse transcriptase polymerase chain reaction (RTPCR) from 3-week-old *Arabidopsis* leaves as described previously (Liao et al., 2004). Two primers covering the whole TSB1 coding region were chosen to amplify a 1413 bp DNA fragment. The 5' primer (5'-GGATCCATGGCAGCCTCAGGCACCTCT3')(SEQ ID NO: 1) and the 3' primer (5-AGATCTTCAAACATCAA-GATATTTAGC3')(SEQ ID NO: 2) were located at the translation initiation site (ATG) and the stop site (TGA) of the TSB1 coding region, respectively. A pfu DNA polymerase (Promega) was used to amplify the DNA fragment to minimize the chance of sequence mutation. The 1413 bp PCR product was cloned into the T7Blue(R) vector (Novagen) to form pT7Blue-TSB1 and the DNA sequence was determined by an ABI PRISM 373 automatic DNA sequencing system. A DNA fragment containing a cauliflower mosaic virus (CaMV) 35S promoter was excised from pBI221 by digestion with HindIII and BamHI and cloned into the HindIII and BamHI site of pCAMBIA 1390 (Center for the Application of Molecular Biology of International Agriculture, Black Mountain, Australia) to form pCAMBIA 1390/35 5. The pCAMBIA 1390 vector contains a selectable marker, hpt gene driven by a 35S promoter. An AtTSB1 cDNA fragment was excised from pT7Blue-TSB1 by digested with BamHI and Bg/II and cloned into the BamHI and Bg/II site of pCMABIA1390/S5S to form pTSB vector (FIG. 1). Plasmid was transformed into *A. tumefaciens* strain GV3101 (pMP9O) cells by electroporation.

Plant Material and Transformation

*Arabidopsis thaliana* (L.) Hyen. ecotype Columbia was grown in controlled environment chambers at 24° C., 70% relative humidity, with 24 h photoperiod (about 120 μmol $m^{-2}s^{-1}$). To transform *Arabidopsis* plants, we used the floral dip method described previously (Clough and Bent, 1998). $T_o$ transgenic plants constitutively expressing AtTSB1, were selected on MS medium with 20 ppm hygromycin (Murashige and Skoog 1962). The sensitivity of wild type and transgenic T2 homozygous seeds (T3 generation) to different concentrations of 5MT and $CdCl_2$ were assessed on the basis of the germination percentage of seedlings at the end of 2 weeks. After standardizing the optimal selection concentration of 5MT and $CdCl_2$, the floral dip transformation was again performed to evaluate the selection efficiency between TSB1 and conventional hydromycin selection systems.

Nucleic Acid Analysis

To identify the positive transformants, genomic DNA from all rooted shoots on MS medium with 20 ppm hygromycin, 75 μM 5MT and 300 μM $CdCl_2$ was extracted as described previously (Hsieh et al., 2002a). The genomic DNA was digested with HindIII and probed with hpt. The total RNA isolation as well as DNA and RNA blot analysis were performed as the method described previously (Hsieh et al., 2002b). The AtTSB1 and hpt genes isolated from pTSB were labeled with ($\alpha$-$^{32}P$) dCTP by the random primer method and used as probes. The 5' primer (5'-ATTCAGATGCCCA-GAAGTCTTGTTC-3') (SEQ ID NO: 3) and the 3' primer (5'-GCAAGTGCTGTGATTTCTTTGCTCA-3') (SEQ ID NO: 4) were chosen to amplify the actin cDNA fragment. The final RT-PCR fragment was cloned into pGEM-T vector to form pGEM/A-actin. The actin cDNA digested from pGEMIA-actin was labeled with ($\alpha^-$-$^{32}P$) dCTP by the random primer method and used as a probe.

Free Trp Content Analysis

Two-week old wild-type and transgenic plants were harvested from germination medium with or without 50 μM 5MT. Endogenous free tryptophan analysis was performed described previously (Edlund et al., 1995) with some modification. Cell extracts were prepared from approximately 50 mg dry weight. Frozen tissues were ground with methanol under continuous shaking for 24 h at 4° C. After centrifuged, the supernatant was filtered by 0.22 μm membrane (Millipore Millexg). The filtered solution was reduced to 1 ml in a Speed Vac concentrator. The final solution was extracted by SEP column (Water Oasis HLB6 cc) and use 1 ml methanol to elute the extracts. Each 100 μl sample was methylated with 160 μl pyridine and 40 μl N-trimethyl-N-trimethylsilyl-trifuoroacetamide at 70° C. for 1 hr. The GC-MS analysis was performed according to conditions described by Edlund et al (Edlund et al., 1995).

Tryptophan Synthase (TS) Activity

Two-week old AtTSB1 transgenic (TM1, TM3 and TM4) and wild-type plants grown under normal conditions were used to determine the TS activity. Plant extracts were prepared by grinding 3-5 g of whole plant tissue in liquid nitrogen. The fine powder was homogenated in 6 ml of 0.1 M potassium phosphate buffer (pH 8.0) and cleared by centrifugation (12,000 g for 15 min at 4 C). The resultant fraction was used as the enzyme extract and activity of TS ($\alpha$ and $\beta$) were performed as described previously (Last et al. 1991).

Results

Generation and Selection of Transgenic Plants on Hygromycin

Figure 2:
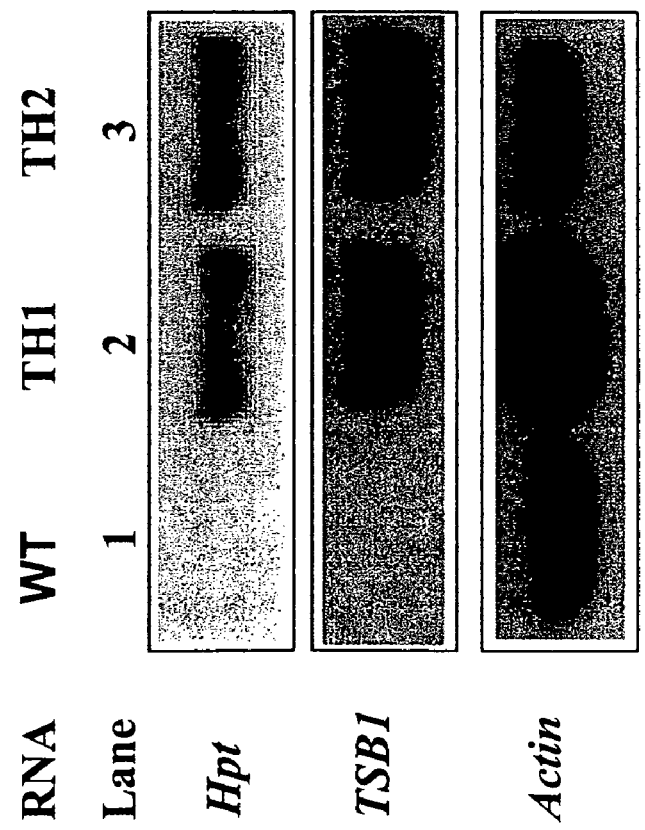
FIG. 2. Transcripts of the AtTSB1 gene expressed in transgenic plants selected by hygromycin. Total RNA (10 µg) was extracted from WT (lane 1) and transgenic plants (THI and TH2). Probes used were $^{32}$P-labeled TSB1, hpt and actin fragment.

The AtTSB1 gene driven by the CaMV 35S promoter was transferred into *Arabidopsis* via *Agro bacterium*-mediated floral-dip method. Seven hygromycin-resistant plants were obtained from 5,400 seeds. All the transgenic plants were confirmed by genomic PCR and Southern blot analyses (data not shown) and designed as TH1 to TH7. Two transgenic $T_2$ homozygous lines, TH1 and TH2, were selected for further analysis. Northern blot analysis was performed to reveal the mRNA level. The hpt mRNA transcripts detected only in the transgenic plants, not in wild-type (FIG. 2, lines 2-3), and a greater accumulation of AtTSB1 mRNA transcripts was observed in all the transgenic plants. The amount of actin mRNA transcripts was similar in both wild-type and transgenic plants.

Figure 3A:
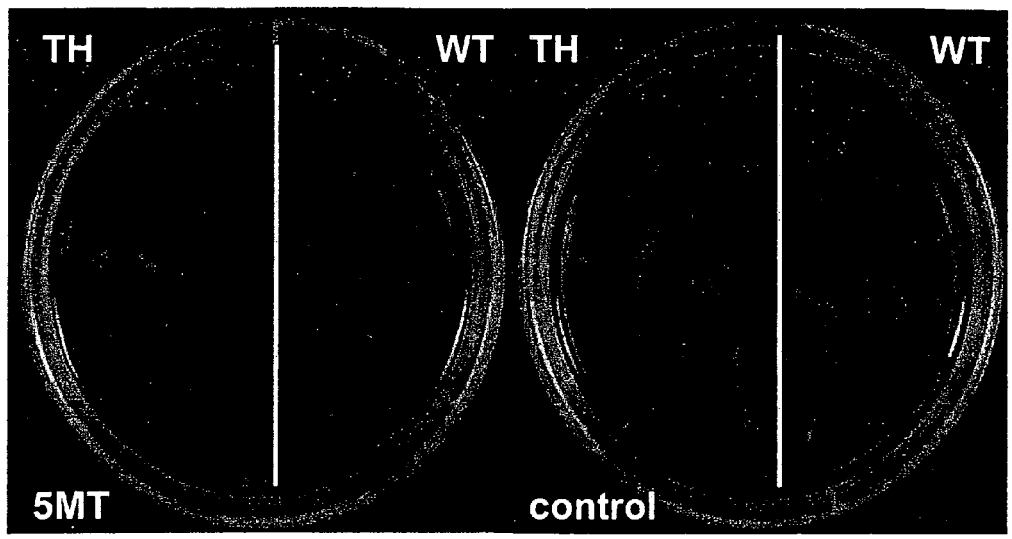
FIG. 3A and 3B. AtTSB1 transgenic Arabidopsis plants are resistant to 5MT and $CdCl_2$. Wild type (WT) did not survive on medium containing 75 µM 5MT (A) and 300 µM $CdCl_2$ (B), whilst transgenic plants (TH) grew on the same medium. Control in panel (A) consisting wild-type and transgenic plants on the medium without 5MT or $CdCl_2$. Plates are 100 mm in diameter.

AtTSB1 Transgenic *Arabidopsis* Seedlings are Resistant to Toxic Trp Analog 5MT and Heavy Metal $CdCl_2$ Seeds of previously selected transgenic homozygous line TH1/TH2 on hygromycin were utilized to demonstrate whether 5MT or $CdCl_2$ can be employed as a selection agent. Different concentrations of 5MT (0, 25, 50, 75, 100 and 200 µM) and $CdCl_2$ (0, 50, 100, 200, 300, 400 and 500 µM) were evaluated in order to select the transformants constitutively expressing AtTSB1 gene and in these experiments untransformed wild-types used as negative control. Sixty seeds of each wild-type and transgenic seeds were germinated on medium containing various concentrations of 5MT for 2 weeks, and the number of surviving plants recorded (Table 1). Under all the tested conditions, both wild-type and transgenic seeds could germinate almost equally. However, after 2 weeks, wild-type plants turned pale green and ceased to grow on medium containing 75 µM and higher (100 and 200 µM) 5MT. In contrast, transgenic seedlings showed resistance to all concentrations of 5MT tested (100 and 200 µM). However, a higher survival rate (100%) was recorded at 75 µM than at other treatments tested (100 and 200 µM) moreover, even after 2 weeks, seedlings displayed enhanced growth than the control wild-type plants (FIG. 3A). In the meantime, all seedlings on medium containing less than 50 µM 5MT survived selection even after 2 weeks. Thus, 75 µM 5MT is the optimum concentration for the selection of putative transformants.

Figure 3B:
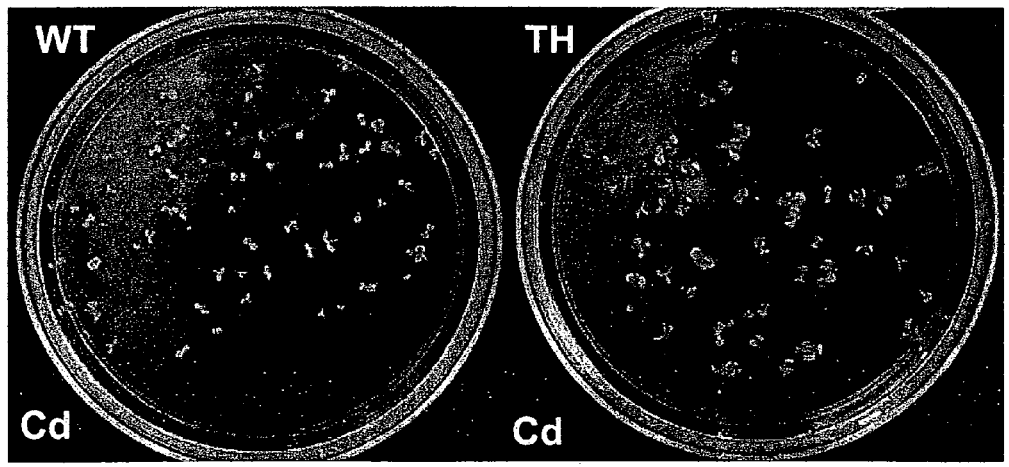

A total of one hundred seeds each of wild-type and transgenic plants were germinated on medium containing different concentrations of $CdCl_2$, for 2 weeks, and the survival was recorded (Table 2). The germination rate in wild-type and transgenic seedlings was almost equal on the medium containing $CdCl_2$ concentrations up to 300 µM. Although the growth of transgenic plants was slightly inhibited at 300 µM $CdCl_2$ after 2 weeks, the overall survival rate was higher than at 400 and 500 µM $CdCl_2$ and most (98%) of the transgenic seedlings were greener than controls (FIG. 3b). All the wild-type and transgenic seedlings survived even after 2 weeks on medium containing $CdCl_2$ less than 100 µM. From these observations, we concluded that 300 µM $CdCl_2$ is the optimal concentration needed for selecting putative transformants.

Figure 4B:
FIG. 4A and 4B. Selection of AtTSB1 putative transformants from seeds collected after floral dip transformation on medium containing 75 µM 5MT (A) and 300 µM $CdCl_2$ (B). The transgenic plants can germinate and grow better on the medium containing 5MT or $CdCl_2$ for 2 weeks.
Figure 4A:
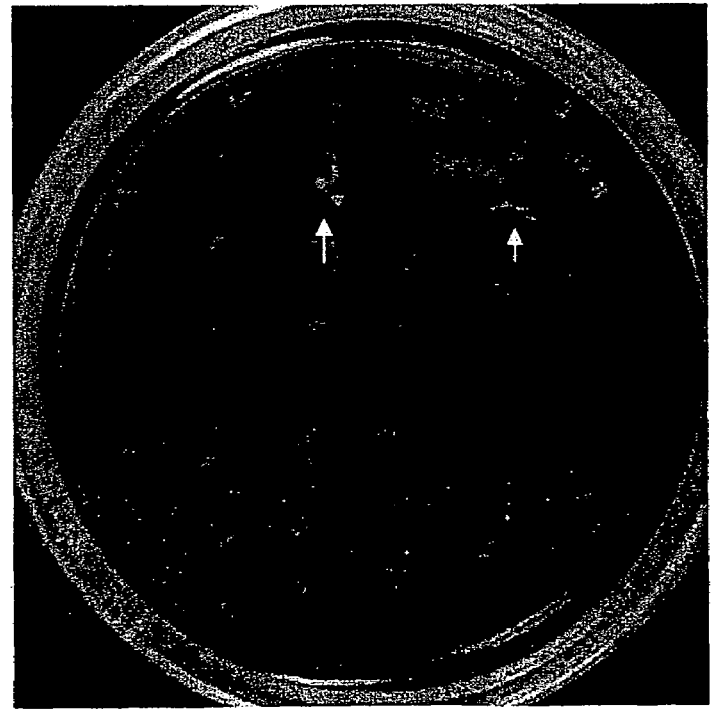

Molecular Analysis of AtTSB1 Transgenic *Arabidopsis* Plants Selected by 5MT and $CdCl_2$ In order to confirm the stable integration and expression of AtTSB1 gene in the genome of the transgenic plants, the AtTSB1 gene was transferred once again into *Arabidopsis* via floral-dip transformation, and putatively transformants were selected on germination medium supplemented with optimum concentrations of 5MT and $CdCl_2$ as selection agents (FIG. 4). Of 5,200 seeds germinated, 6 putative transgenic, designated as TM1 to TM6, were obtained on 5MT selection, and three plants (TM1, TM3 and TM4) were randomly selected for further molecular and biochemical analyses. Of 5,850 seeds, about 8 putative transgenic plants, designated TC 1 to TC8, were obtained on $CdCl_2$ and four plants (TC2, TC3, TC4 and TC5) were randomly selected for further analyses. All putative transgenic plants selected were transferred to soil to allow for continued normal growth and development.

Figures 5A, 5B:
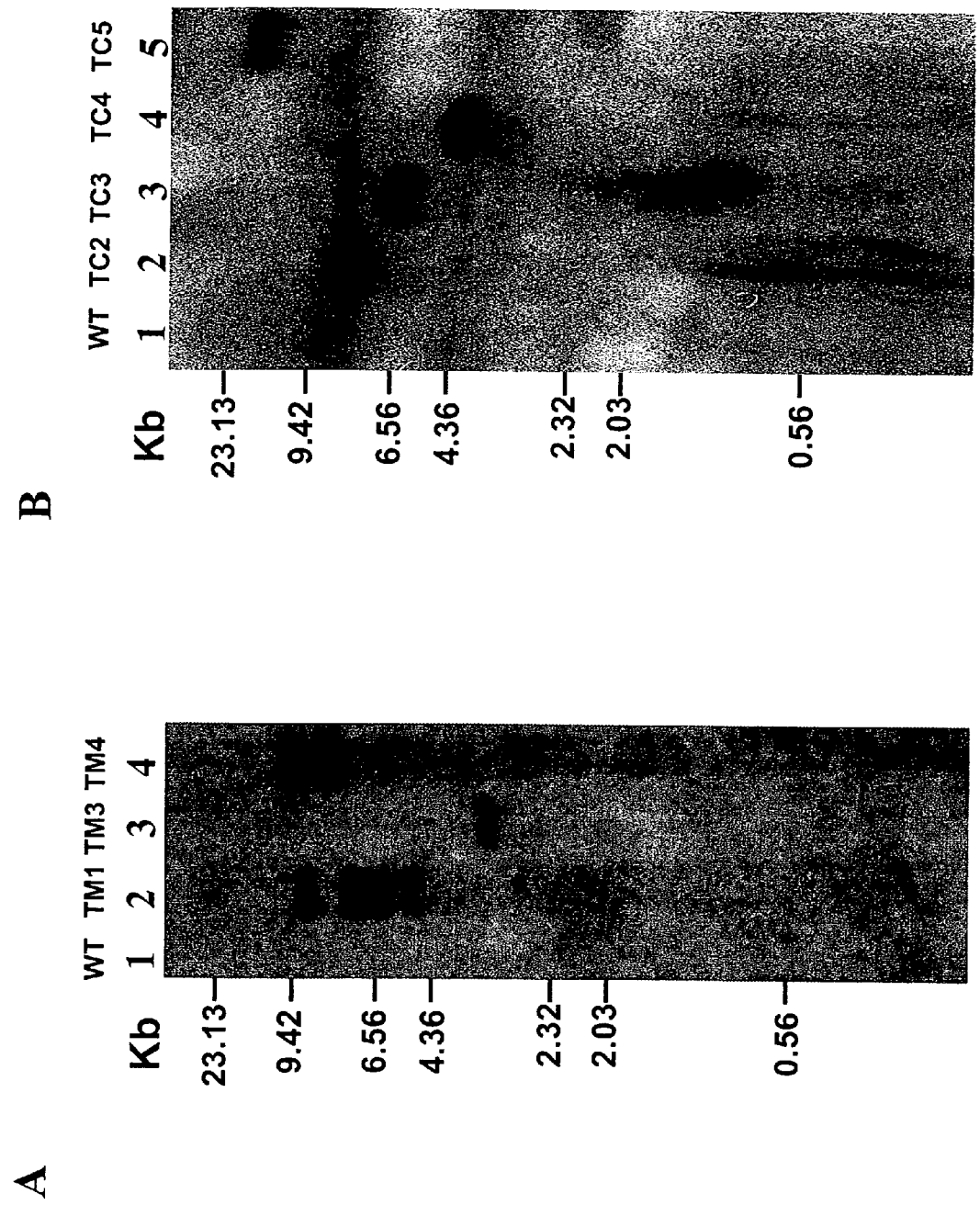
FIG. 5A and 5B. Molecular acid analyses of wild-type and AtTSB1 transgenic plants selected by 5MT and $CdCl_2$. (A) Southern blot analysis of wild-type and transgenic plants selected by 5MT. Lane 1 DNA from a wild-type (WT) plant, lane 2-4 DNA from transgenic plants (TMI, TM3 and TM4). (B) Southern blot analysis of wild-type and transgenic plants selected by $CdCl_2$. Lane 1 DNA from a wild-type (WT) plant, lanes 2-4 DNA from transgenic plants (TC2, TC3, TC4 and TC5). Probe used was $^{32}$P-labeled hpt.
Figure 6B:
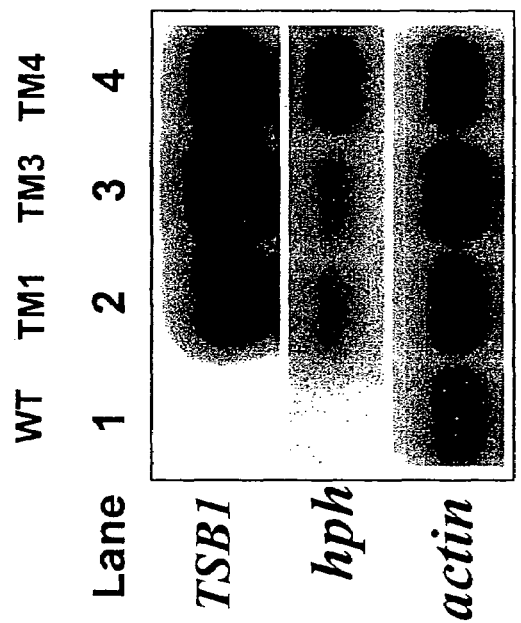
FIG. 6A and 6B. Elevated mRNA transcripts levels in AtTSB1 transgenic plants. (A) Northern blot analysis of transgenic plants selected by 5MT. Total RNA (10 µg) was extracted from WT (lane 1) and transgenic plants (TM 1, TM3 and TM4). (B) Northern blot analysis of transgenic plants selected by $CdCl_2$. Total RNA (5 µg) was extracted from WT (lane 1) and transgenic plants (TC2, TC3, TC4 and TM5). Probes used were $^{32}$P-labeled TSBJ, hpt and actin fragment. rRNA was used as internal control.
Figure 6A:
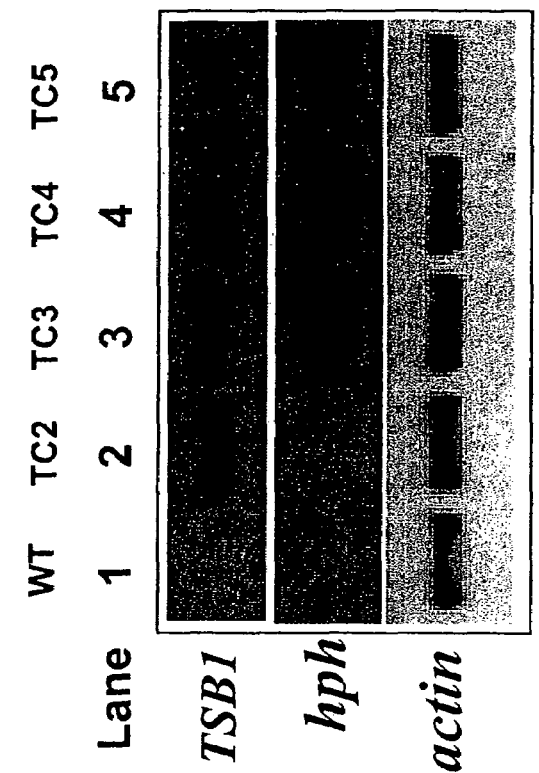

To confirm their transgenic nature, all the putative transgenic plants were further assayed by Southern blot analysis (FIG. 5a, b). Total genomic DNA isolated from the leaves of the transgenic and wild-type plants, was digested with Hind III and probed with hpt gene. Multiple insertion of transgene was observed in TMI and TM4 (lanes 2 and 4 in FIG. 5A), whereas, single gene integration of size 3.5 kb was observed in TM3 (lane 3 in FIG. 5A). As shown in FIG. 5b, the four $CdCl_2$-tolerant transgenic plants (TC2, TC3, TC4 and TC5) revealed a single copy transgene insertion of size 4 and 18 kb in TC4 and TC5, respectively (lane 4 & 5 in FIG. 5B). In another parallel experiment, one of the putative transgenic plants, TC7, did not show any signal on either PCR or Southern blot analyses (data not shown). Thus, isolated chances of escape may exists in the $CdCl_2$ selection. All together, these results confirmed the efficient selection of putative transformants by use of 5MT and $CdCl_2$ and integration of the AtTSB1 gene in the genome of transgenic *Arabidopsis* plants.

Transgenic Plants Selected by 5MT and $CdCl_2$ are Expressed High TSB1 Transcripts Transgenic plants TMI, TM3, TM4, TC2, TC3, TC4 and TC5 selected by 5MT and $CdCl_2$, were tested for AtTSB1 gene expression by Northern blot analyses using TSB1 and hpt as probes in an independent experiments. TSB1 mRNA transcripts were highly expressed in all the transgenic lines tested (lanes 2-4 in FIG. 6A; lanes 2-5 in FIG. 6b). No signal was observed in wild-type; however, the long-term exposed x-ray films displayed endogenous TSB1 mRNA transcripts. The hpt mRNA transcripts were detected in all the transgenic plants TM1, TM3 and TM4 (lanes 2-4 in FIG. 6a), however, uneven expression level was observed among the tested transgenic plants. Interestingly, even hpt mRNA transcripts were detected in transgenic plants, TC3, TC4 and TC5 (lanes 3-5 in FIG. 6B), but no transcripts were detected in TC2 (lane 2 in FIG. 6b) and wild-type. These results indicated that the AtTSB1 transgene was sufficiently expressed in all the transgenic plants and hence imparted resistance to toxic 5MT and $CdCl_2$.

Comparison of Selection Efficiency between the Conventional and TSB1 Systems

The selection efficiency of the TSB1 system was compared with conventional antibiotic selection system using hygromycin in a parallel experiment. The selection efficiency on hygromycin, 5MT and $CdCl_2$ is depicted in Table 3. On hygromycin, 7 putative transgenic plants were obtained out of 5,400 seeds. On 5MT and $CdCl_2$6, 8 putative transformants were selected out of 5,200 and 5,850 seeds, respectively, after floral-dip transformation. All the putative transgenic plants were confirmed by genomic PCR and Southern blot analysis (data not shown). Thus, the transgenic selection efficiency in the TSB1 is comparable to that of the conventional negative selection system.

AtTSB1 Transgenic Plants Accumulate High Level of Free Trp Content than Wild-Type To elucidate the possible relation between the accumulation of free Trp content and resistance to 5MT and $CdCl_2$, free Trp content was measured in AtTSB1 transgenic plants. As shown in Table 4, the level of free Trp was higher in AtTSB1 transgenic plants than in wild-type plants with or without 5MT/$CdCl_2$. The level in the transgenic plants TM1, TM3 and TM4 was 10- to 15-fold higher (5,900-8,900 pmole/g dry weight) than in wild-type plants (587 pmole/g dry weight). The presence of 5MT in the medium greatly reduced the level of free Trp (almost fivefold) in wild-type plants (125 pmole/g dry weight), but that in transgenic plants was maintained at a steady level (5,100-7,200 pmole/g dry weight). A similar trend was observed when TC3, TC4 and TC5 transgenic plants were measured for Trp content, with or without CdCl2. These results demonstrated a greater accumulation of free Trp in AtTSB1 transgenic *Arabidopsis* plants and a greater resistance to 5MT and CdCl2 than control plants.

Figures 7A, 7B:
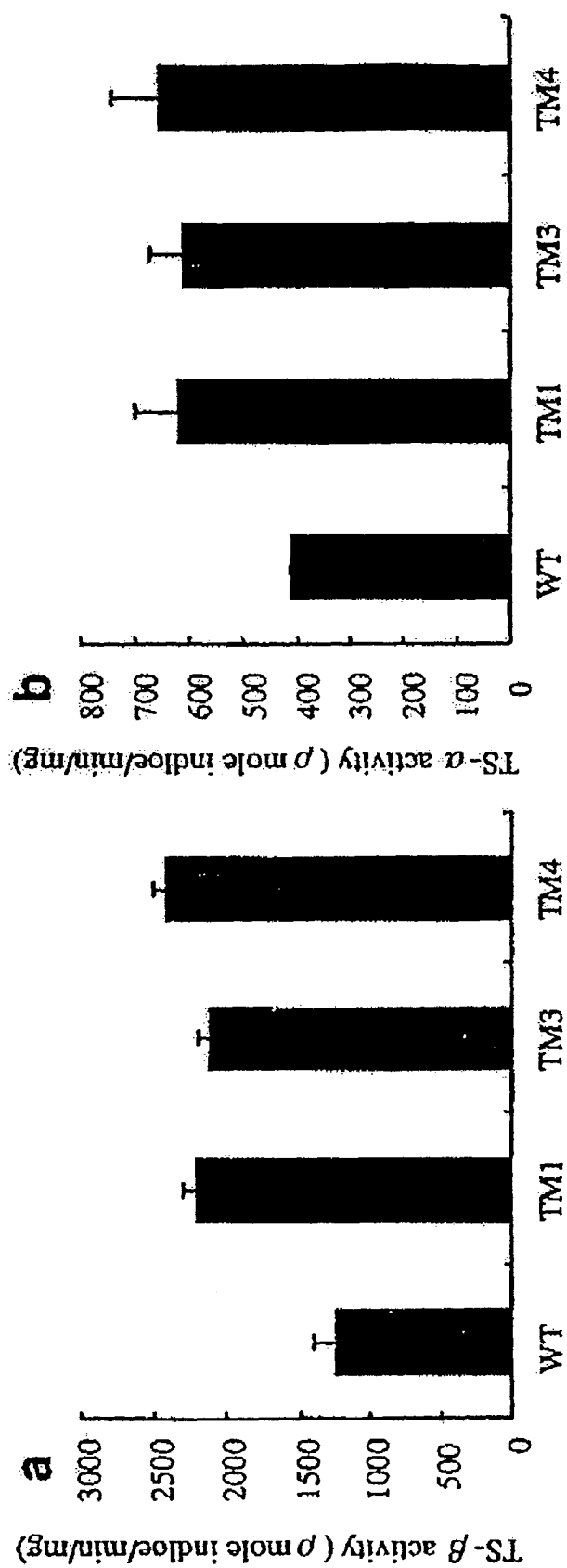
FIG. 7A and 7B. Analysis of the activity of tryptophan synthase (TS) in 2-week-old AtTSB1 transgenic (TM 1, TM3, TM4) and wild-type (WT) plants. (A) The activity of TS-β in the AtTSB1 transgenic and WT plants. (B) The activity of TS-α in the AtTSB1 transgenic and WT plants. Enzymes were assayed from the crude plant extracts. Specific activities are presented in picomoles of indole converted per minute per milligram of protein for TS activity (n=3).

Increased Activity of Tryptophan Synthase-β and Tryptophan Synthase-β in AtTSB1 Transgenic Plants We measured the activity of tryptophan synthase-β (TS-β) in 2-week-old AtTSB1 transgenic (TM1, TM3 and TM4) and wild-type plants grown under normal conditions. The activity of TS-β in all the AtTSB1 transgenic plants was almost double than control plants (FIG. 7a). However, overexpression of AtTSB1 moderately increased the activity of TS-α in transgenic plants (FIG. 7b). These results clearly demonstrated that the overexpression of TSB1 gene in *Arabidopsis* proportionately increased the activity of TS-α and β.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

REFERENCES

Avonce, N., Leyman, B., Mascorro-Gallardo, J. O., Van Dijck, P., Thevelein, J. M., and Iturriaga, G (2004). The *Arabidopsis* trehalose-6-P synthase AtTPS1 gene is a regulator of glucose, abscisic acid, and stress signaling. Plant Physiol 136, 3649-3659.

Breitler, J. C., Meynard, D., Van Boxtel, J., Royer, M., Bonnot, F., Cambiliau, L., and Guiderdoni, E. (2004). A novel two T-DNA binary vector allows efficient generation of marker-free transgenic plants in three elite cultivars of rice (*Oryza sativa* L.). Transgenic Res 13, 27 1-287.

Chan Y L, Lin K H, Sanjaya, Liao L J, Chen W H, Chan M T (2005). Gene stacking in *Phalaenopsis* orchid enhances dual tolerance to pathogen attack. Transgenic Res 14:279-288.

Cho, H. J., Brotherton, J. E., and Widholm, J. M. (2004). Use of the tobacco feedback-insensitive anthranilate synthase gene (ASA2) as a selectable marker for legume hairy root transformation. Plant Cell Rep 23, 104-113.

Cho, H. J., Brotherton, J. E., Song, H. S., and Widholm, J. M. (2000). Increasing tryptophan synthesis in a forage legume *Astragalus sinicus* by expressing the tobacco feedback-insensitive anthranilate synthase (ASA2) gene. Plant Physiol 123, 1069-1076.

Clough, S. J., and Bent, A. F. (1998). Floral dip: a simplified method for *Agrobacterium*-mediated transformation of *Arabidopsis thaliana*. Plant J 16, 735-743.

Daniell H, Muthukumar B, Lee S B (2001a) Marker free transgenic plants: engineering the chloroplast genome without the us of antibiotic selection. Curr Genet 39:109-116.

Daniell H, Wiebe P O, Millan A F (2001a) Antibiotic-free chloroplast genetic engineering—an environmentally friendly approach. Trends Plant Sci 6:237-239.

de Vetten, N., Wolters, A. M., Raemakers, K., van der Meer, I., ter Stege, R., Heeres, E., Heeres, P., and Visser, R. (2003). A transformation method for obtaining marker-free plants of a cross-pollinating and vegetatively propagated crop. Nat Biotechnol 21, 439-442.

Ebmeier, A., Allison, L., Cerutti, H., and Clemente, T. (2004). Evaluation of the *Escherichia coli* threonine deaminase gene as a selectable marker for plant transformation. Planta 218, 751-758.

Edlund, A., Ekiof, S., Sundberg, B., Moritz, T., and Sandberg, G (1995). A Microscale Technique for Gas Chromatography-Mass Spectrometry Measurements of Picogram Amounts of Indole-3-Acetic Acid in Plant Tissues. Plant Physiol 108, 1043-1047.

Erikson, O., Hertzberg, M., and Nasholm, T. (2004). A conditional marker gene allowing both positive and negative selection in plants. Nat Biotechnol 22, 455-458.

Erikson, O., Hertzberg, M., and Nashoim, T. (2005). The dsdA gene from *Escherichia coli* provides a novel selectable marker for plant transformation. Plant Mol Biol 57, 425-433.

Haldrup, A., Petersen, S., and Okkels, F. (1998a). Plant xylose isomerase gene from *Thermoanaerobacterium thermosulfurogenes* allows effective selection of transgenic plant cells using D-xylose as the selection agent. Plant Mol Biol 37, 287-296.

Haldrup, A., Petersen, S. G, and Okkels, F. T. (1998b). Positive selection: a plant selection principle based on xylose isomerase, an enzyme used in the food industry. Plant Cell Rep 18:76-81.

Hsieh, T. H., Lee, J. T., Charng, Y. Y., and Chan, M. T. (2002a). Tomato plants ectopically expressing *Arabidopsis* CBF 1 show enhanced resistance to water deficit stress. Plant Physiol 130, 618-626.

Hsieh, T. H., Lee, J. T., Yang, P. T., Chiu, L. H., Charng, Y. Y., Wang, Y. C., and Chan, M. T. (2002b). Heterology expression of the *Arabidopsis* C-repeat/dehydration response element binding factor 1 gene confers elevated tolerance to chilling and oxidative stresses in transgenic tomato. Plant Physiol 129, 1086-1094.

Hull, A. K., Vij, R., and Celenza, J. L. (2000). *Arabidopsis* cytochrome P450s that catalyze the first step of tryptophan-dependent indole-3-acetic acid biosynthesis. Proc Natl Acad Sci USA 97, 2379-2384.

Joersbo, M. (2001). Advances in the selection of transgenic plants using non-antibiotic marker genes. Physiologia Plantarum 111, 269-272.

Kanno, T., Kasai, K., Ikejiri-Kanno, V., Wakasa, K., and Tozawa, V. (2004). In vitro reconstitution of rice anthranilate synthase: distinct functional properties of the alpha subunits OASAI and OASA2. Plant Mol Biol 54, 11-22.

Kisaka H, Kisaka M, Lee H Y, Kmeya T (1998) Isolation of a cDNA for tryptophan Synthase β from rice and studies of its expression in a 5-methyltryptophan-resistant mutant of rice. Plant Mol Biol 38:875-878.

Last, R. L., Bissinger, P. H., Mahoney, D. J., Radwanski, E. R., and Fink, G R. (1991). Tryptophan mutants in *Arabidopsis*: the consequences of duplicated tryptophan synthase beta genes. Plant Cell 3, 345-358.

Leyman, B., Avonce, N., Ramon, M., Van Dijck, P., Thevelein, J. M., and Iturriaga, G-(2004). New selection marker for plant transformation. Methods Mol Biol 267, 385-396.

Leyman, B., Avonce, N., Ramon, M., Dijck, P. V., Iturriaga, G, and Thevelein, J. M. (2005). Trehalose-6-phosphate synthase as an intrinsic selection marker for plant transformation. J Biotechnol.

Liao, L.-J., Pan, I. C., Chan, Y.-L., Hsu, Y.-H., Chen, W.-H., and Chan, M.-T. (2004). Transgene silencing in *Phalaenopsis* expressing the coat protein of Cymbidium Mosaic Virus is a manifestation of RNA-mediated resistance. Molecular Breeding 13:229-242.

Mentewab A, Stewart C N Jr (2005) Overexpression of an *Arabidopsis thaliana* ABC transporter confes kanamycin resistance to transgenic plants. Nat Biotechnol 23:1177-1180

Miki, B., and McHugh, 5. (2004). Selectable marker genes in transgenic plants: applications, alternatives and biosafety. J Biotechnol 107:193-232.

Pomponi M, Censi V, Di Girolamo V, De Paolis A, di Toppi L. S., Aromolo R, Costantino P, Cardarelli M (2006) Overexpression of *Arabidopsis* phytochelatin synthase in tobacco plants enhances Cd(2+) tolerance and accumulation but not translocation to the shoot. Planta 223:180-190.

Pruitt, K. D., and Last, R. L. (1993). Expression patterns of duplicate tryptophan synthase beta genes in *Arabidopsis thaliana*. Plant Physiol 102, 10 19-1026.

Taulavuori, K., Prasad, M. N., Taulavuori, E., and Lame, K. (2005). Metal stress consequences on frost hardiness of plants at northern high latitudes: a review and hypothesis. Environ Pollut 135, 209-220.

Tian L, Jordan M, Miki B (2006) Markers ad selector genes for plant transformation. In: Jaime A Teixeira da Silva (eds) Ornamental an plant biotechnology, vol II. Global Science Books, London, pp 9-20.

Tian L (2006) Markers gene removal from transgenic plants. In: Jaime A Teixeira da Silva (eds) Ornamental and plant biotechnology, vol II. Global Science Books, London, pp 26-29.

Tozawa, Y., Hasegawa, H., Terakawa, T., and Wakasa, K. (2001). Characterization of rice anthranilate synthase alpha-subunit genes OASAI and OASA2. Tryptophan accumulation in transgenic rice expressing a feedback-insensitive mutant of OASAI. Plant Physiol 126, 1493-1506.

Tsai, F. Y., Brotherton, J. E., and Widholm, J. M. (2005). Overexpression of the feedback-insensitive anthranilate synthase gene in tobacco causes tryptophan accumulation. Plant Cell Rep 23, 548-556.

Wenck, A., and Hansen, G (2005). Positive selection. Methods Mol Biol 286, 227-236.

You S J, Liau C H, Hauang H E, Feng T Y, Prasad V, Hsiao HH, Lu J C, Chan M T (2003) Sweet pepper ferredoxin-likeprotein (pflp) gene as a novel selection marker for orchid transformation. Planta 217:60-65.

Zhao, Y., Christensen, S. K., Fankliauser, C., Cashman, J. R., Cohen, J. D., Weigel, D., and Chory, J. (2001). A role for flavin monooxygenase-like enzymes in auxin biosynthesis. Science 291, 306-309.

All references cited herein are incorporated by reference.

TABLE 1

Variation in seedling survival rate of wild-type and transgenic *Arabidopsis* with 5MT concentration

| Conc. | WT | | TH | |
|---|---|---|---|---|
| (μM) | 1 week | 2 weeks | 1 week | 2 weeks |
| 0 | 60/60 | 60/60 | 60/60 | 60/60 |
| 25 | 60/60 | 24/60 | 60/40 | 60/60 |
| 50 | 60/60 | 10/60 | 40/40 | 60/60 |
| 75 | 60/60 | 0/60 | 60/60 | 60/60 |
| 100 | 25/60 | 0/60 | 60/60 | 34/60 |
| 200 | 12/60 | 0/60 | 60/60 | 18/60 |

WT: wild type,
TH: transgenic plant.

TABLE 2

Variation in seedling survival rate of wild-type and transgenic *Arabidopsis* with $CdCl_2$ concentration

| Conc. | WT | | TH | |
|---|---|---|---|---|
| (μM) | 1 week | 2 weeks | 1 week | 2 weeks |
| 0 | 100/100 | 100/100 | 100/100 | 100/100 |
| 50 | 100/100 | 100/100 | 100/100 | 100/100 |
| 100 | 100/100 | 100/100 | 100/100 | 100/100 |
| 200 | 100/100 | 30/100 | 100/100 | 95/100 |
| 300 | 80/100 | 0/100 | 100/100 | 98/100 |
| 400 | 12/100 | 0/100 | 100/100 | 80/100 |
| 500 | 8/100 | 0/100 | 100/100 | 62/100 |

WT: wild type,
TH: transgenic plant.

TABLE 3

Comparison of the selection efficiency of transgenic *Arabidopsis* by hygromycin, 5MT and $CdCl_2$

| Selection agent | After transformation seed germination | No. of seedling surviving on MS | No. of transgenic plants | Transformation efficiency (%) |
|---|---|---|---|---|
| 5MT | 5,200 | 6 | 6 | 0.12 |
| $CdCl_2$ | 5,850 | 8 | 7 | 0.12 |
| HS | 5,400 | 7 | 7 | 0.13 |

5MT: 5'-methyl-tryptophan,
HS: hygromycin selection.

TABLE 4

Endogenous contents of tryptophan in wild-type and TSB transgenic plants with or without 5-methyl-tryptophan

| | tryptophan (pmole/g g · DW) |
|---|---|
| wild type | 587 ± 5 |
| TM1 | 6,100 ± 4 |
| TM3 | 5,900 ± 12 |
| TM4 | 8,900 ± 21 |
| wild type + 5MT | 125 ± 6 |
| TM1 + 5MT | 5,200 ± 14 |
| TM3 + 5MT | 5,100 ± 11 |
| TM4 + 5MT | 7,200 ± 10 |

5MT concentration: 50 μM

What is claimed is:

1. A selection system comprising (i) a DNA construct comprising a promoter, a trytophan synthase beta 1 (TSB1) gene, and a genetic modification, wherein the TSB1 gene and the genetic modification are promoted by the same promoter, and (ii) $Cd^{+2}$-containing medium for use in selecting a plant transfected with the DNA construct.

2. The selection system of claim 1, wherein the DNA construct's promoter is a CaMV35S promoter.

3. The selection system of claim 1, wherein the DNA construct's genetic modification is Tnos (nopaline synthase terminator sequence).

4. A method of selecting a plant transfected with a DNA construct comprising a promoter, a trytophan synthase beta 1 (TSB1) gene, and a genetic modification, wherein the TSB1 gene and the genetic modification are promoted by the same promoter, comprising the steps of: contacting the plant with a composition comprising $Cd^{+2}$ or a mixture $Cd^{+2}$ and 5MT (5 methyl tryptophan); and determining
   a) whether the plant survives;
   b) whether the plant's tryptophan synthase activity is greater than that of the wild type plant contacted with the same composition; or
   c) whether the plant's free tryptophan concentration is greater than that of the free tryptophan concentration in the wild type plant.

5. The method of claim 4, wherein the DNA construct's promoter is a CaMV 35S promoter.

6. The method of claim 4, wherein the DNA construct's genetic modification is Tnos (nopaline synthase terminator sequence).

* * * * *

SEQUENCE LISTING

<160> NUMBER OF SEQ ID NOS: 4

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggatccatgg cagcctcagg cacctct                                          27

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agatcttcaa acatcaagat atttagc                                          27

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
attcagatgc ccagaagtct tgttc                                            25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcaagtgctg tgatttcttt gctca                                            25